(12) United States Patent
Jahnke et al.

(10) Patent No.: US 10,398,301 B2
(45) Date of Patent: Sep. 3, 2019

(54) METHOD AND SYSTEM FOR COGNITIVE FUNCTION TESTING

(71) Applicant: EYEGUIDE, INC., Lubbock, TX (US)

(72) Inventors: Nathan A. Jahnke, Lubbock, TX (US); J. Brian Still, Wolfforth, TX (US); Gregory L. Gamel, Lubbock, TX (US); Benedicto C. Baronia, Lubbock, TX (US)

(73) Assignee: EYEGUIDE, INC., Lubbock, TX (US)

( * ) Notice: Subject to any disclaimer, the term of this patent is extended or adjusted under 35 U.S.C. 154(b) by 300 days.

(21) Appl. No.: 15/240,642

(22) Filed: Aug. 18, 2016

(65) Prior Publication Data
US 2017/0049373 A1 Feb. 23, 2017

Related U.S. Application Data

(60) Provisional application No. 62/207,445, filed on Aug. 20, 2015.

(51) Int. Cl.
*A61B 5/16* (2006.01)
*A61B 5/00* (2006.01)
(Continued)

(52) U.S. Cl.
CPC .......... *A61B 3/0025* (2013.01); *A61B 3/0041* (2013.01); *A61B 3/0083* (2013.01);
(Continued)

(58) Field of Classification Search
CPC ... A61B 3/0025; A61B 3/0041; A61B 3/0083; A61B 3/0091; A61B 3/113; A61B 3/145; A61B 3/152; A61B 5/4088
See application file for complete search history.

(56) References Cited

U.S. PATENT DOCUMENTS 4,528,989 A 7/1985 Weinblatt
8,602,789 B2 12/2013 Hallowell et al.
(Continued)

FOREIGN PATENT DOCUMENTS

WO 2009111426 9/2009
WO 2015/048839 A1 4/2015

OTHER PUBLICATIONS

International Search Report and Written Opinion for PCT Application No. PCT/US2016/047578, dated Nov. 21, 2016.
(Continued)

*Primary Examiner* — Sean P Dougherty
*Assistant Examiner* — Nicholas E Kolderman
(74) *Attorney, Agent, or Firm* — Mark E. Scott; Dickinson Wright PLLC

(57) ABSTRACT

Cognitive function testing. At least some of example embodiments are methods including performing a cognitive function test on a patient without calibrating pupil position of the patient. The performing may include: causing a visual cue on a computer screen in front of the patient to move in a predetermined pattern; reading frames from an eye camera that captures images of an eye of the patient while the visual cue moves on the computer screen and the patient visually tracks the visual cue; determining pupil position within the frames; correcting offsets between the stimulus data and the pupil position data; translating the pupil position data from a coordinate space of the eye camera to a coordinate space of the stimulus data; and generating a test score being the cumulative distance between the stimulus data and pupil position data for each corresponding point in time.

35 Claims, 11 Drawing Sheets

(51) Int. Cl.
  *A61B 3/113* (2006.01)
  *A61B 3/00* (2006.01)
  *A61B 3/14* (2006.01)
  *G06F 3/01* (2006.01)
  *A61B 10/00* (2006.01)

(52) U.S. Cl.
  CPC ............ *A61B 3/0091* (2013.01); *A61B 3/113* (2013.01); *A61B 3/145* (2013.01); *A61B 5/4088* (2013.01); *G06F 3/013* (2013.01); *A61B 5/0022* (2013.01); *A61B 2010/0009* (2013.01)

(56) References Cited

U.S. PATENT DOCUMENTS

| | | |
|---|---|---|
| 8,860,660 B2 | 10/2014 | Jahnke |
| 2003/0012425 A1 | 1/2003 | Suzuki et al. |
| 2004/0015098 A1 | 1/2004 | Souvestre |
| 2006/0200013 A1* | 9/2006 | Smith ................ A61B 5/14532 600/319 |
| 2006/0270945 A1 | 11/2006 | Ghajar |
| 2007/0013868 A1 | 1/2007 | Pugach et al. |
| 2011/0205167 A1 | 8/2011 | Massengill |
| 2013/0176534 A1* | 7/2013 | Frankfort ............... A61B 3/113 351/209 |
| 2013/0308099 A1* | 11/2013 | Stack ..................... A61B 3/113 351/209 |
| 2014/0154650 A1* | 6/2014 | Stack ..................... A61B 5/162 434/236 |
| 2014/0255888 A1* | 9/2014 | Stack ..................... A61B 5/162 434/236 |
| 2015/0062534 A1* | 3/2015 | Massengill .......... A61B 5/4064 351/209 |

OTHER PUBLICATIONS

Examination Report dated Dec. 4, 2018 in corresponding Canadian Application No. 2,996,148; 4 pages.
Extended Search Report dated Apr. 18, 2019 in corresponding European Application No. 16837847.9; 9 pages.

* cited by examiner

METHOD AND SYSTEM FOR COGNITIVE FUNCTION TESTING

CROSS-REFERENCE TO RELATED APPLICATIONS

This application claims the benefit of U.S. Provisional Application Ser. No. 62/207,445 filed Aug. 20, 2015 and titled "Eye Tracking Concussion Detection." This provisional application is incorporated by reference herein as if reproduced in full below.

BACKGROUND

Lifelong effects of concussions, particularly concussions incurred in childhood, have been discovered in recent years. These effects may include memory loss, depression, and dementia, to name a few. One of the issues with concussion detection is the amount of equipment and time it takes to provide a clinician with suitable information from which to diagnose the concussion. For example, many concussion symptom detection systems require specialized facilities (e.g., special rooms with precisely controlled lighting) or expensive and bulky equipment (e.g., CAT scan equipment, MRI equipment). Other concussion detection systems are time consuming, such as the ImPACT Test, a written examination administered by computer a predetermined amount of time (e.g., hours) after an injury, with the result compared to pre-injury performance on the same written examination.

Some concussion symptom detection systems are also susceptible to manipulation. For example, for written examinations an athlete (anticipating possible concussion during the season but not wanting to lose playing time) may intentionally perform poorly on a pre-injury written examination so as to mask the degradation of post-injury performance on the same written examination. Moreover, given that the written examination questions may be freely available, an athlete may further attempt to skew the post-injury written examination results by studying and/or memorizing the examination questions and answers prior to application of the post-injury written examination.

For related-art concussion symptom detection systems that track eye movement, the manipulation happens during calibration of pupil position to gaze location. That is, related-art concussion symptom detection systems first calibrate pupil position to gaze location on the screen by having the patient stare intently at a plurality of predetermined locations on the screen, and from the relationship between pupil position and the predetermined locations a calibration is determined. The athlete manipulates the results of the initial testing by intentionally not looking directly at the predetermined locations, thus skewing the pre-injury testing to lower performance levels.

BRIEF DESCRIPTION OF THE DRAWINGS

For a detailed description of exemplary embodiments, reference will now be made to the accompanying drawings in which.

NOTATION AND NOMENCLATURE

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"About" in reference to a value shall mean the recited value (e.g., distance, rotation) plus or minus 5% of the recited value.

"Lemniscate pattern" shall mean a curve of a figure eight pattern, but shall not require any particular underlying mathematical form.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The example embodiments are directed to methods and systems of cognitive function testing, including testing for symptoms of concussion. The example cognitive function testing discussed below can be performed quickly compared to related-art systems, such as a test of about 10 seconds or less with results immediately available. Moreover, the example cognitive function testing is less susceptible to manipulation. The chances of manipulation are lower because the testing is performed without calibrating pupil position of the patient to gaze location on the computer screen used to perform the test. Moreover, the cognitive function testing of the various embodiments is in the form of smooth eye pursuit, and while gaze location can be controlled consciously, smooth eye pursuit is difficult to intentionally manipulate. Thus, the possibility of manipulation of baseline testing is reduced or eliminated. The specification first turns to example systems to implement the specific technical solution, and then to the methods implemented by those specific systems.

Figure 1:
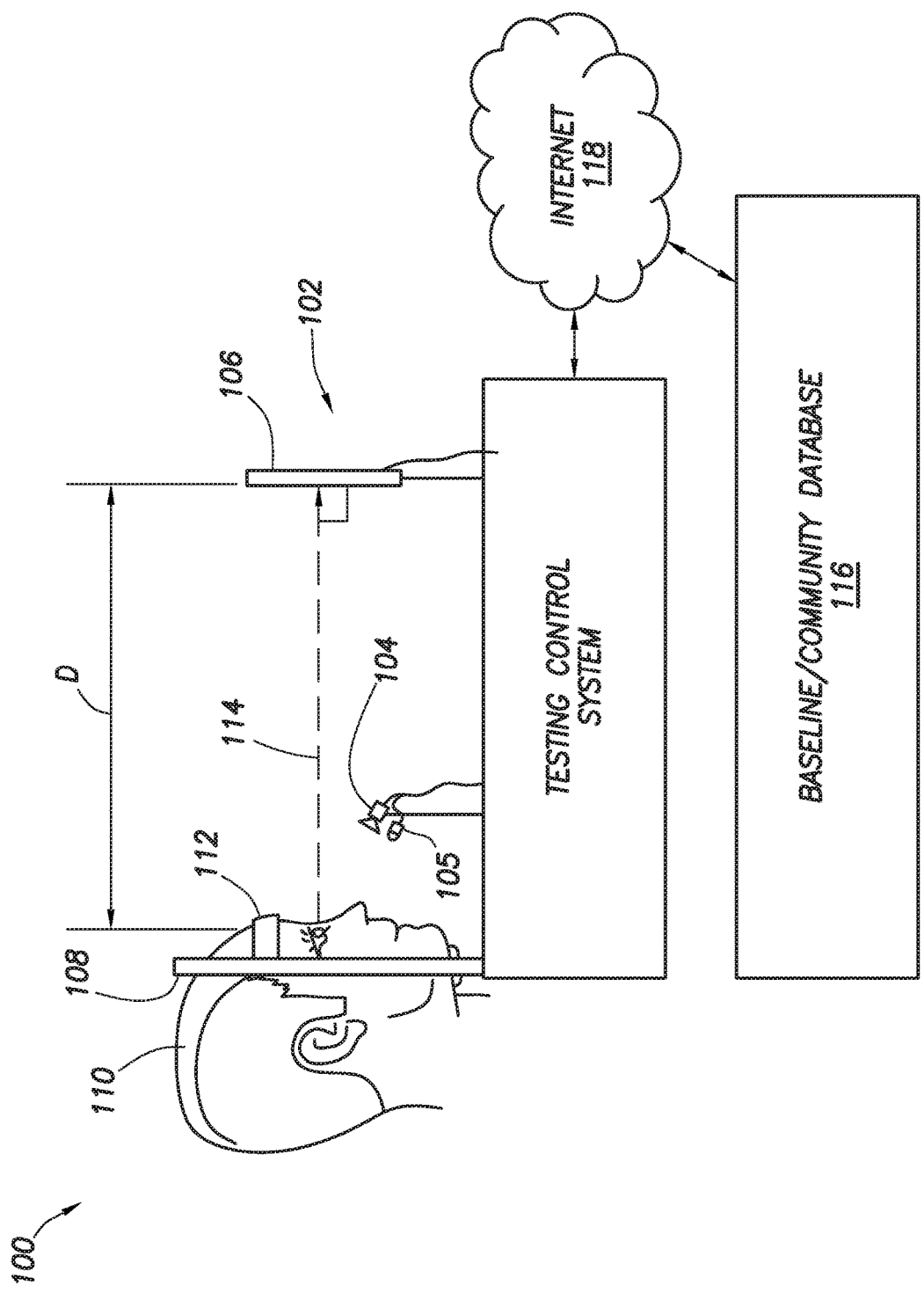
FIG. 1 shows a system in accordance with example embodiments.

FIG. 1 shows an example system 100 for performing cognitive function testing. In particular, the system 100 comprises testing control system 102 including an eye camera 104 and a computer screen 106. The testing control system 102 is also associated with a device to immobilize the head of a patient 110, the device to immobilize the patient's head illustratively shown as a chin rest 108. In use, the chin of a patient 110 is placed on the chin rest 108, and the patient's head is placed against the head strap 112. In example systems, the distance D from eyes of the patient 110 to the computer screen is about two feet for a computer screen 106 having a size of 1024 by 768 pixels; however, the distance may be shorter for smaller screens, and the distance may be longer for larger screens. Such a distance and screen size combination provides a wide range of eye movement for the cognitive function testing, but the exact distance is not critical. For cases where the cognitive function testing is based on a pre-injury or baseline test for the particular patient (discussed more below), the distance D should be about the same for the baseline test and the post-injury test.

Further with respect to placement of the computer screen 106, the computer screen 106 is placed such that, when the patient is looking directly forward, a line of sight 114 of the patient is at about the center of the computer screen 106. Stated otherwise, relative elevation of the patient's eyes and a center of the computer screen may be about the same. Moreover, the angle of the front surface of the computer screen 106 is adjusted such that the front surface of the computer screen is substantially perpendicular to the line of sight 114. However, elevational differences as between the patient's eyes and the center of the computer screen, as well as rotational offsets of the computer screen, can be accounted for in the example calculations as discussed more below.

The eye camera 104 may be placed above or below the line of sight 114 of the patient 110, and in the example system of FIG. 1 the eye camera 104 is placed below the line of sight. The eye camera 104 is adjusted such that, during a cognitive function test, the eye camera 104 captures frames of one of the patient's eyes, and in most cases frames of the dominate eye of the patient. In some example embodiments, the eye camera 104 is associated with one or more infrared light emitting diodes 105 (LEDs, discussed more below) directing infrared energy toward the patient's eye, and the eye camera 104 has an optical filter that filters visible light but allows reflected infrared light to pass to the charge-coupled device (CCD) array of the eye camera 104. Use of filters and infrared LEDs reduces glare and unwanted reflections from other light sources, such as lighting in a room where the cognitive function test is performed, or stadium lights if the cognitive function test is performed outdoors.

Still referring to FIG. 1, the example testing control system 102 is communicatively coupled to a database 116 by way of a computer network 118, illustratively shown as the Internet (hereafter just Internet 118). The database 116 may store indications of cognitive function from previous tests of either the patient, the community at large, or both. As will be discussed in greater detail below, determining whether the patient has symptoms of concussion (or other malady resulting in loss of cognitive function) may be based on an indication of cognitive function of a baseline test for the patient. In yet still other cases, the indication of cognitive function may be based on a set of community standards generated from baseline testing of a set of patients within the community, and again the community standards may be stored on the database 116. Further still, the indication of cognitive function may be based on both the baseline testing for the particular patient and a number of standard deviations the post-injury score changes from the baseline (with the standard deviations determined based on community baselines). In other example systems, the baseline testing scores and community averages may be stored within the testing control system 102 such that communicative coupling to remote databases is not implemented or only periodically implemented.

Figure 2:
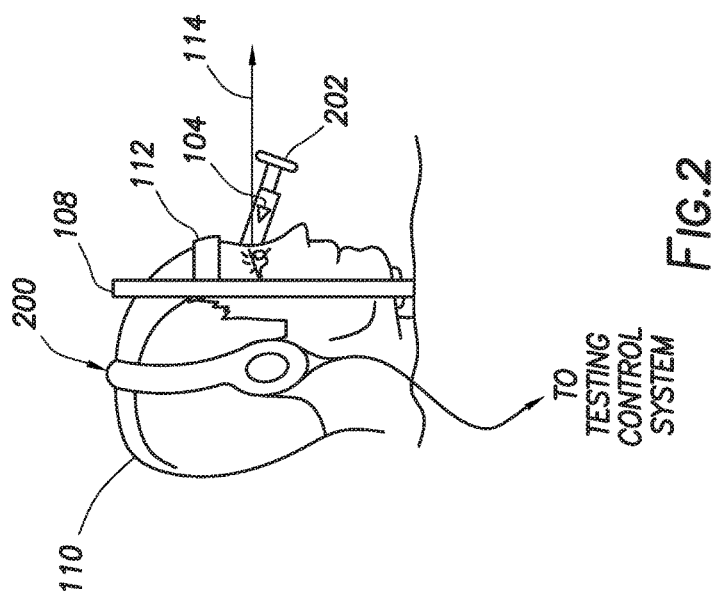
FIG. 2 shows a partial system in accordance with example embodiments.

FIG. 2 shows a partial alternate embodiment. In particular, in FIG. 2 the eye camera 104 is associated with a headset 200. That is, the patient 110 puts on the headset 200, and then the patient 110 places his head in the chin rest 108, including abutting the forehead against the head strap 112. In the example headset 200 of FIG. 2, the eye camera 104 views the eye by way of a reflective lens 202, and because of the example reflective lens 202 the frames captured are from below the line of sight 114. Thus, FIG. 2 shows a portion of an example system where the eye camera is functionally and communicatively coupled to the testing control system 102, but the eye camera need not be rigidly coupled to the testing control system 102.

Figure 3:
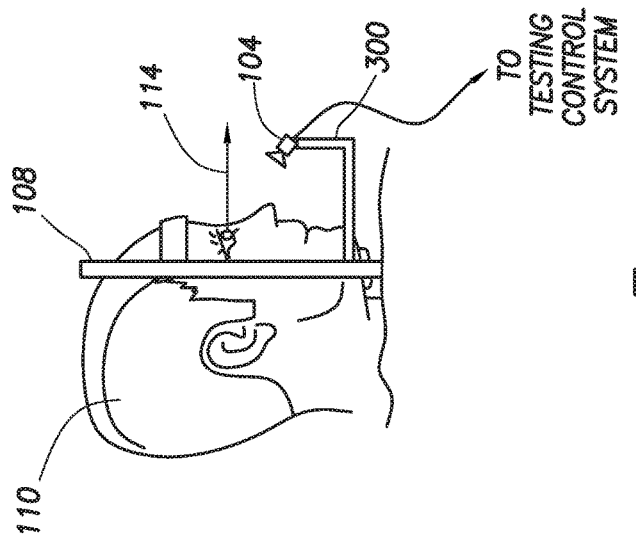
FIG. 3 shows a partial system in accordance with example embodiments.

FIG. 3 shows yet another partial alternative embodiment. In particular, in FIG. 3 the eye camera 104 is coupled to the chin rest 108 by way of a rigid arm member 300. That is, the patient 110 places his head in the chin rest 108, including abutting the forehead against the head strap 112, and the eye camera 104 is held below the line of sight 114 by the rigid arm 300. Thus, FIG. 3 shows a portion of an example system where the eye camera is functionally and communicatively coupled to the testing control system 102, but the eye camera being part of the chin rest 108. The specification now turns to example specific hardware that may be used to implement portions of the method aspects of the various embodiments.

Figure 4:
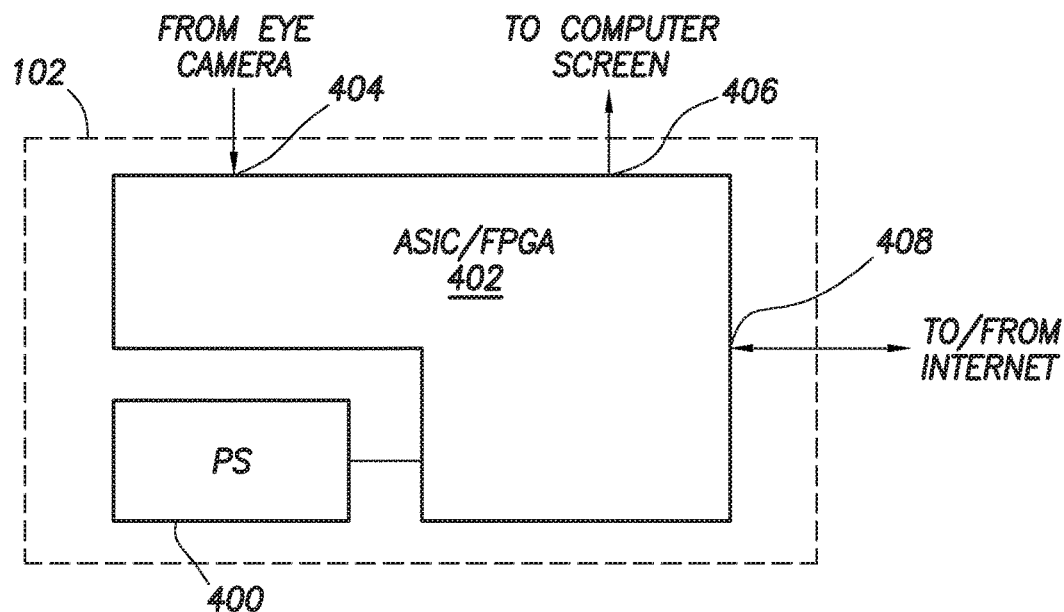
FIG. 4 shows a block diagram of a testing control system in accordance with example embodiments.

FIG. 4 shows, in block diagram form, an example testing control system 102. In particular, the testing control system 102 of FIG. 4 comprises a power supply 400 ("PS" in the drawing). The power supply 400 may be a converter that converts alternating current (AC) power from a wall socket to direct current (DC) power, the power supply 400 may comprise a battery and switching converter to create particular voltages, or some combination thereof. The power supply 400 in the example systems provides power to a specific integrated circuit 402 designed specifically to implement the various methods and functionality of the cognitive function testing system 100 (FIG. 1). That is, in mass production, and to reduce product costs, at least some of the functionality and control aspects may be implemented in the specific integrated circuit, such as an Application Specific Integrated Circuit (ASIC), a Field Programmable Gate Array (FPGA), or combination devices specifically configured to perform the control and testing. Thus, the specific integrated circuit 402 is communicatively coupled to the eye camera 104 (FIG. 1) by way of a first port 404, the computer screen 106 (FIG. 1) by a second port 406, and the Internet 118 (FIG. 1) by a third port 408. One having ordinary skill in the art, with the benefit of this disclosure, could specify functionality for configuring the specific integrated circuit 402, including implementing portions in analog hardware.

Figure 5:
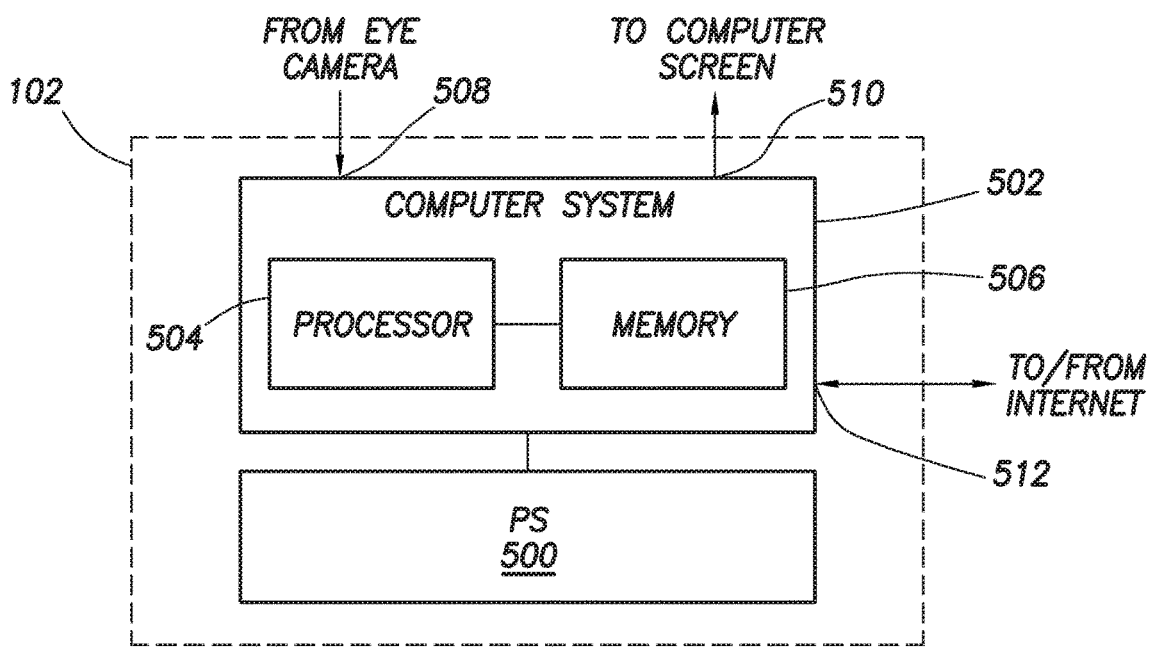
FIG. 5 shows a block diagram of a testing control system in accordance with example embodiments.

FIG. 5 shows, in block diagram form, another example testing control system 102. In particular, the testing control system 102 of FIG. 5 comprises a power supply 500. Like the power supply 400, the power supply 500 may be a converter that converts AC power from a wall socket to DC power, the power supply 500 may comprise a battery and switching converter to create particular voltages, or some combination thereof. The power supply 500 in the example systems provides power to a specific system 502 designed, constructed, and programmed to implement the cognitive function testing. In the example system the specific system 502 may comprise a computer system including a processor 504 coupled to memory 506. The memory may store instructions executed by the processor 504 to implement the calculation aspects of the cognitive function testing, discussed more thoroughly below. The specific system 502 is designed to implement the various methods and functionality of the cognitive function testing system 100 (FIG. 1). Thus, the specific system 502 may be communicatively coupled to the eye camera 104 (FIG. 1) by way of a first port 508, the computer screen 106 (FIG. 1) by a second port 510, and the Internet 118 (FIG. 1) by a third port 512.

Figure 6:
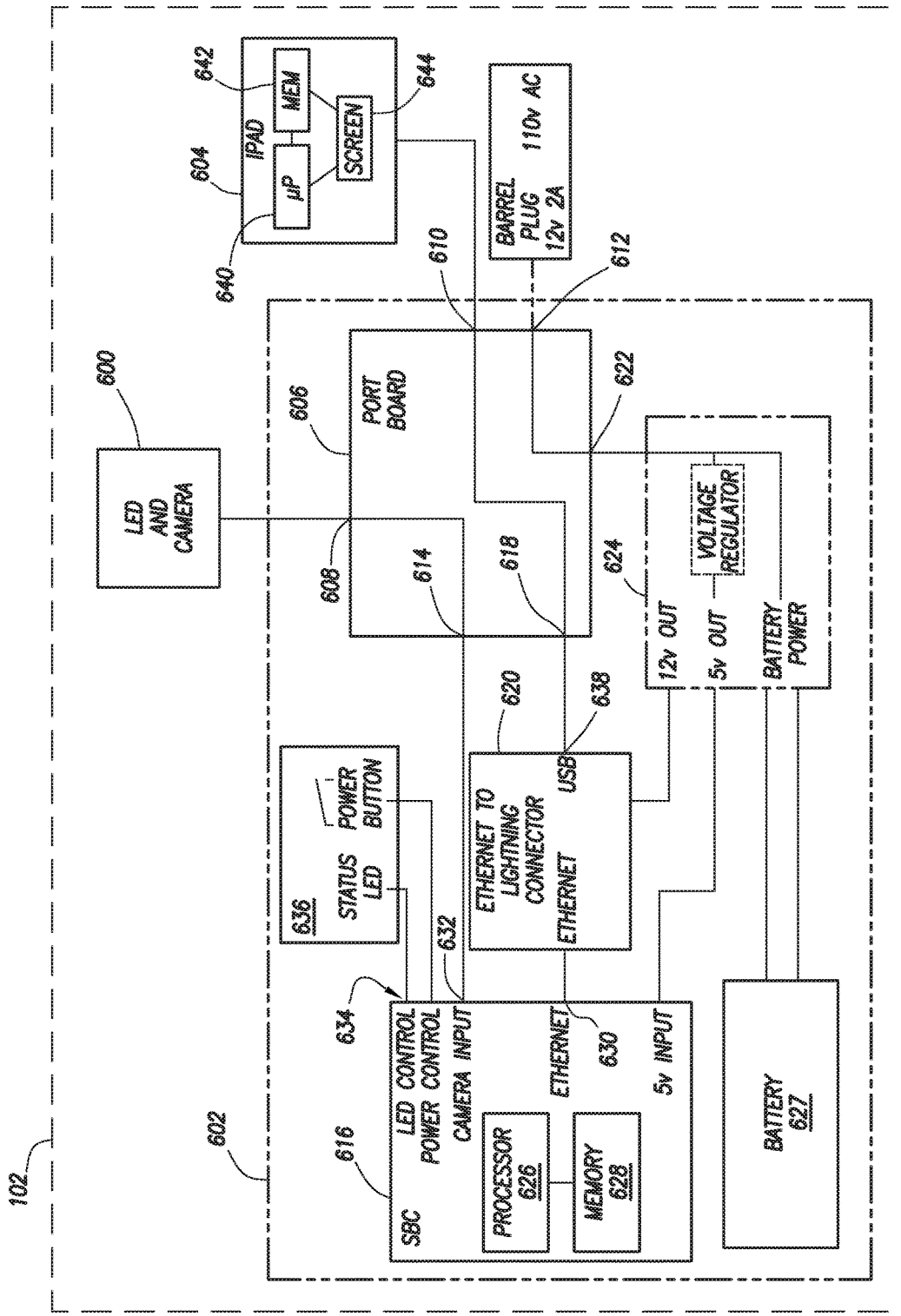
FIG. 6 shows a block diagram of a testing control system in accordance with example embodiments.

The various embodiments of the testing control system 102 discussed to this point, particularly the ASIC and FPGA implementations, assume large-scale production runs to reduce overall hardware costs. However, other implementations are possible. FIG. 6 shows a testing control system 102 that represents the developmental system, and further the initial production system of the overall cognitive function testing system 100 (FIG. 1). The balance of the discussion will be based on the testing control system 102 of FIG. 6 with the understanding that the developmental context shall not be read as a limitation as to the various possible hardware implementations.

The testing control system 102 of FIG. 6 can be conceptually divided into three components: an eye camera system 600; an eye camera pack 602; and a portable computer 604. Each conceptual component will be addressed in turn. The eye camera system 600 comprises the eye camera 104 (FIG. 1, not specifically shown in the block diagram of FIG. 6) and one or more LEDs. In one example system, the LEDs are configured to direct infrared energy toward the eye of the patient to provide infrared illumination of the eye during cognitive function testing. Likewise, in example systems where the LEDs produce infrared energy, the eye camera of the eye camera system 600 has an optical filter to remove light from the visible spectrum. The LEDs and eye camera implemented in the camera system 600 of FIG. 6 may be those described in commonly owned U.S. Pat. No. 8,860,660, the full disclosure of which is incorporated by reference herein as if reproduced in full below.

The eye camera pack 602 is a series of components used to interface with the eye camera system 600, and to provide pupil position data to the portable computer 604. In the example of FIG. 6, the eye camera pack 602 comprises port board 606 that implements various physical communication ports. In the example system, the port board 606 implements a video port 608 which communicatively couples to the camera system 600. In one example embodiment, the video port 608 is implemented in the form factor of a mini display port, but the pin assignments modified to accommodate not only communicative coupling to the camera system 600, but also to provide power to the LEDs. Other form factor ports may be equivalently used. The port board 606 further comprises an interconnect port 610 that may be used to communicatively couple to the portable computer 604. In the example system, the port board 606 implements an interconnect port 610 in the form factor of a Universal Serial Bus (USB). Other form factors may be equivalently used. Further, the example port board 606 implements a power port 612 that may be used to couple to power, such as power "bricks" that convert AC power available at wall sockets to DC. In the example system, the port board 606 implements a power port 612 in the form factor of a barrel plug. Other form factors may be equivalently used.

Still referring to FIG. 6, and particularly the port board 606, the port board 606 implements corresponding internal connections to various components. For example, the video port 608 may be communicatively coupled to an internal video connector 614, which in the example case may be implemented as a flexible flat cable (FFC) connector coupled to a single board computer (SBC) 616 (the single board computer discussed in greater detail below). The interconnect port 610 may be communicatively coupled to an internal communication connector 618 coupled to a protocol conversion board 620 (the protocol conversion board discussed in greater detail below). Finally, the port board 606 may feed power from the power port 612 to an internal power connection 622 coupled to voltage regulation board 624 (discussed more below). In some cases the port board 606 is merely a pass through device, providing interconnections based on different form factors. In other embodiments, however, the port board 606 may provide additional functionality, such as voltage protection, filtering, signal amplification, and the like.

The eye camera pack 602 may also implement a voltage regulation board 624. In the example system, the voltage regulation board 624 receives, in some situations, power from the external power source (as shown in FIG. 6). In other situations, however, the voltage regulation board 624 receives power from an internal battery 627, and passes through, converts, and/or regulates the power from the battery 627 to various voltages and currents used for devices within the eye camera pack 602. In the example system, the voltage regulation board 624 creates a 5 Volt (V) power signal applied to the single board computer 616, and provides a 12 V power signal to the protocol conversion board 620.

Still referring to FIG. 6, the example eye camera pack 602 further implements a single board computer 616. In one example embodiment, the single board computer 616 may be Raspberry Pi single board computer system developed by the Raspberry Pi Foundation and available from several sources, such as Digi-Key Electronics of Thief River Falls, Minn. The single board computer 616 implements a processor 626 and memory 628. The example single board computer 616 implements an Ethernet port 630, a camera input port 632, various LED and control ports 634, as well as additional components not specifically shown. The LED and control ports 634 couple to an example power and status board 636, where the power and status board 636 provides visual indications of the state of the eye camera pack 602, as well externally accessible power control buttons (shown but not specifically numbered). The single board computer 616 couples to the eye camera of the eye camera system 600 by way of the camera input port 632. In the example system the camera input port 632 may be implemented as a flat flexible connector, and thus the camera input port 632 couples to the port board 606 such that the video port in the example mini display port form may be provided externally by the port board 606.

In the example system, the single board computer 616 also couples portable computer 604 by way of the Ethernet port 630. In the example system the portable computer 604 may be implemented in the form of an IPAD® brand device available from Apple Inc. of Cupertino, Calif. The portable computer 604 in the form of an IPAD® does not have a wired Ethernet connection, and thus in the example system the Ethernet port 630 of the single board computer 616 couples to the protocol conversion board 620. The protocol conversion board 620, in turn, couples by way of an example USB port 638 to the port board 606. The protocol conversion board 620 performs protocol translation (both Ethernet to Lightning, and vice-versa) and thus enables two way communications between the single board computer 616 and the portable computer 604. In cases where the portable computer 604 implements a hard-wired Ethernet port, the protocol conversion board may be omitted. Finally, the single board computer 616 couples to the voltage regulation board 624 and receives operational power therefrom.

Still referring to FIG. 6, the testing control system 102 further comprises a portable computer 604. The portable computer 604 comprises a processor 640 coupled to a memory 642. The memory stores data structures, as well as programs executed by the processor 640 to implement portions of the cognitive function testing. The portable computer 604 also has a computer screen coupled to the processor 640. It is on the computer screen 640 that the visual cue may be moved as part of the cognitive function testing. As noted above, the portable computer 604 may be an IPAD® device in some example systems.

The specification now turns to a description of the cognitive function testing of the various embodiments. Reference will be made to the example testing control system 102 of FIG. 6 to describe the interaction of the various components and to further specify how the various processors contribute to the overall testing. Again, however, it will be understood that FIG. 6 represents one example specifically implemented system, and thus reference to FIG. 6 shall not be read as a limitation.

Figure 7:
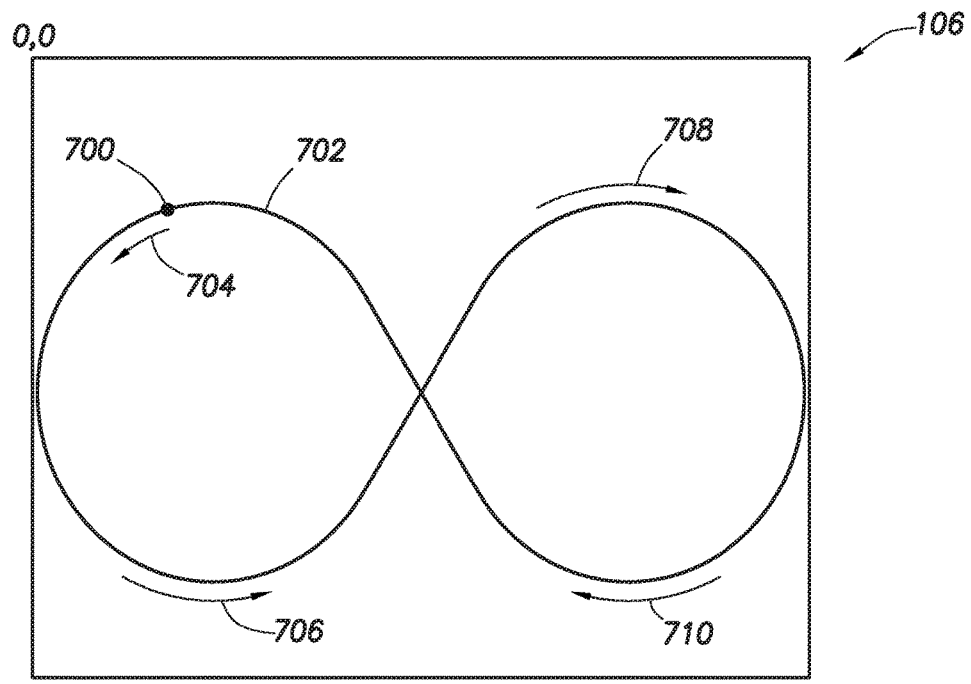
FIG. 7 shows an example computer screen as viewed by the patient during a cognitive function test in accordance with example embodiments.

FIG. 7 shows an example computer screen 106 as viewed by the patient during a cognitive function test in accordance with various embodiments. In particular, during an example cognitive function test the computer screen 106 is oriented in a landscape configuration. Provided on the computer screen 106 is a visual cue 700. In some cases the visual cue 700 is pure white solid-fill circle having a diameter of 5 pixels, the pure white circle against a black background, but other color schemes may be equivalently used. In the example cognitive function test the visual cue 700 initially appears as circle in what will be the left lobe of a lemniscate pattern (i.e., a "lazy" figure eight pattern) to be traced out by the visual cue 700. In FIG. 7, the lemniscate pattern is shown as line 702, however it will be understood that the line 702 is not visible to the patient and is provided here merely for ease of description of the pattern the visual cue 700 traces out. In the example system, simultaneous with the appearance of the visual cue 700 on the computer screen 644 of the portable computer 604, the portable computer 604 also sends a command to the eye camera pack 602 to begin the testing procedure. The description will first describe functions of the portable computer 604 during the visual portion of the example cognitive function testing, then turn to the functions of the eye camera pack 602 simultaneously performed with the visual portions, and then to functions the portable computer 604 performs with the data created.

During the cognitive function test, under control of the portable computer 604 the visual cue 700 appears and initially traces down and to the left as indicated by arrow 704. In one example system, during travel the visual cue 700 abuts the left-most portion of the computer screen 106. That is, when the visual cue 700 abuts the left-most portion of the computer screen, the left-most portion of the visual cue 700 is made up of pixels in the left-most column of pixels of the computer screen 106. Although not required, the inventors of the current specification have found that having the visual abut the left-most portion (and as described more below the right-most portion on opposite side of the lemniscate pattern) adds a level of complexity to the cognitive function testing because such a method tests the patient's ability to anticipate the trajectory of the visual cue given the uncertainty provided by the edge of the computer screen. The visual cue 700 of the example cognitive function testing then continues to trace out the lemniscate pattern as shown by arrow 706, and then arrow 708. As the visual cue traces out the downward travel path on the right lobe of the lemniscate pattern, again in the example systems the visual cue abuts the right-most portion of the computer screen 106. The process of tracing out the lemniscate pattern continues, as shown by arrow 710. In the example system, the visual cue is visible on the screen for ten seconds, but longer and shorter visibility times are also contemplated. Moreover, in the example system the visual cue 700 moves at a speed to trace out the lemniscate pattern about 1.43 times. That is, the visual cue 700 moves at speed slightly faster than needed to traverse the lemniscate pattern in ten seconds. Faster and slower speeds of the visual cue 700 are also contemplated. During periods of time when the visual cue is visible and moving, the testing control system 102 (and in the case of FIG. 6 the computer system 604) creates stimulus data being the position of the visual cue on the computer screen as a function of time. The stimulus data may be coded in any suitable fashion, such as a series of data points, each data point having X,Y position coordinates and a corresponding time stamp, or a single (beginning or end) time stamp associated with position coordinates such that the time associated with each individual position coordinate can be calculated.

During periods of time of when visual cue 700 is visible and moving on the computer screen, the testing control system 102 (and in the case of FIG. 6, the eye camera pack 602) is configured to read frames from the eye camera 104 capturing images of the eye while the patient visually tracks the visual cue 700. In some systems, the frames of the eye camera 104 may be captured at the rate of between and including 60 and 120 frames per second, but slightly slower and faster capture rates may be equivalently used. At significantly slower frame capture rates, the cognitive function testing accuracy declines, and at significantly faster frame capture rates the performance gain asymptotically approaches theoretical asymptote, and in practice testing control system 102 performance may begin to decline.

In the example system of FIG. 6, the single board computer 616 reads frames from the eye camera system 600 by way of the camera input port 632. Depending on the processing ability of the single board computer 616, the single board computer 616 may first gather all the frames for the cognitive function test, and then once all the frames are gathered the single board computer 616 then determines pupil center positions (hereafter just "pupil position") within each frame. In other cases, the single board computer 616 may simultaneously read the frames and determine pupil position within each frame. Regardless of the timing of the determining pupil position, the testing control system creates pupil position data being the pupil position within the frames of eye camera as a function of time. That data may be coded in any suitable fashion, such as a series of data points, each data point having X,Y position coordinates and a corresponding time stamp, or a single (beginning or end) time stamp associated with position coordinates such that the time associated with each individual position coordinate can be determined.

In accordance with example systems, pupil position is determined for each frame for frames recorded at 60 frames per second for a test of about 10 seconds, which in theory results in 600 pupil positions. However, due to hardware issues (e.g., time slicing between threads on a processor, scheduling of threads in multi-threaded processors, clock skew between independently running systems), software issues (e.g., erroneous pupil tracking, transmission delays), and the fact the patient may blink during the testing, fewer than 600 pupil positions may be determined for any given cognitive function test. In order to address variances in the number of pupil positions determined, in example systems the pupil positions falling within the first and final seconds of the cognitive function test are discarded. Discarding the pupil center positions falling within the first and final seconds of the cognitive function test results in about eight seconds of data, or about 480 pupil positions. Further in the example systems, and in order to make the later calculations consistent, pupil position data are then discarded one datum at a time until 477 pupil positions remain. In the example system the pupil position data are discarded starting at the beginning (in time) of the pupil position data, but any discarding scheme may be used (e.g., discarding starting at the end (in time) of the data). Discarding to arrive at 477 points of pupil position may be implemented in the example system of FIG. 6 by either the eye camera pack 602 prior to transferring the data points to the portable computer 604, or the portable computer 604 may discard the data points after the un-reduced pupil position data has been transferred from the eye camera pack 602. Thus, in example systems capturing images of the eye at 60 frames per second, the further processing is based on 477 points of pupil position data as a function of time. In other systems capturing images of the eye at 120 frames per second, the further processing is based on 954 points, with the discarding to arrive at 954 implemented similarly.

The stimulus data represents the position of the visual cue 700 in the coordinate space of the computer screen 106 as a function of time. The coordinate space of the computer screen 106 is a two-dimensional space, and by convention the pixel at the upper-left corner is designated as location (X=0, Y=0), with Y values increasing down the computer screen, and X values increasing to the right on the computer screen. However, the pupil position data (in the example system generated by the single board computer 616 of the eye camera pack 602) is in the coordinate space of the eye camera 104. Moreover, because the eye camera 104 captures images from other than directly in front of the eye (e.g., below the pupil), the pattern of pupil positions may be distorted with larger upper portions of the lobes of the lemniscate pattern, and smaller lower portions. Moreover, if the eye camera 104 is positioned left or right of the eye during recording the frames, the pattern of pupil positions may be distorted with one lobe being smaller than the other lobe. Whether the left lobe or the right lobe is smaller depends on position of the camera relative to the eye, as well as whether the camera is capturing frames of the eye directly or by way of a reflective surface. Because the eye camera may not match the patient's face rotationally, the pattern of pupil positions may be angularly rotated from a horizontal lemniscate pattern. Finally, the patient's eye moves in three dimensions because of the eye's generally circular nature, and thus the pattern of pupil positions may be distorted based on the pupil position data effectively being a projection of the three dimensional movement of the pupil into the two-dimensional coordinate space of the eye camera.

In some of the example systems, for example the system of FIG. 6, there may be different clock domains. That is, the example single board computer 616 has its own free-running clock, and the portable computer 604 has its own free running clock. Even if the time between the two clocks is synchronized at an earlier point in time before the cognitive function testing, the time within each clock domain may differ because of skew. Moreover, in systems with separately running processors performing different tasks, the portable computer 604 sends a start command to the single board computer 616 to begin the process of reading frames and determining pupil position; however, because of transmission delays and delays associated with the processors in time-sliced and/or multithreaded systems, the time alignment between the stimulus data and the pupil position data may be off. The problem may be further exacerbated if the communicative coupling between the eye camera pack 602 and the portable computer 604 is a wireless (e.g., IEEE 802.11) connection, which wireless connection may experience varying latency based on the number of users, and the number of networks in the vicinity, to name a few.

Figure 8:
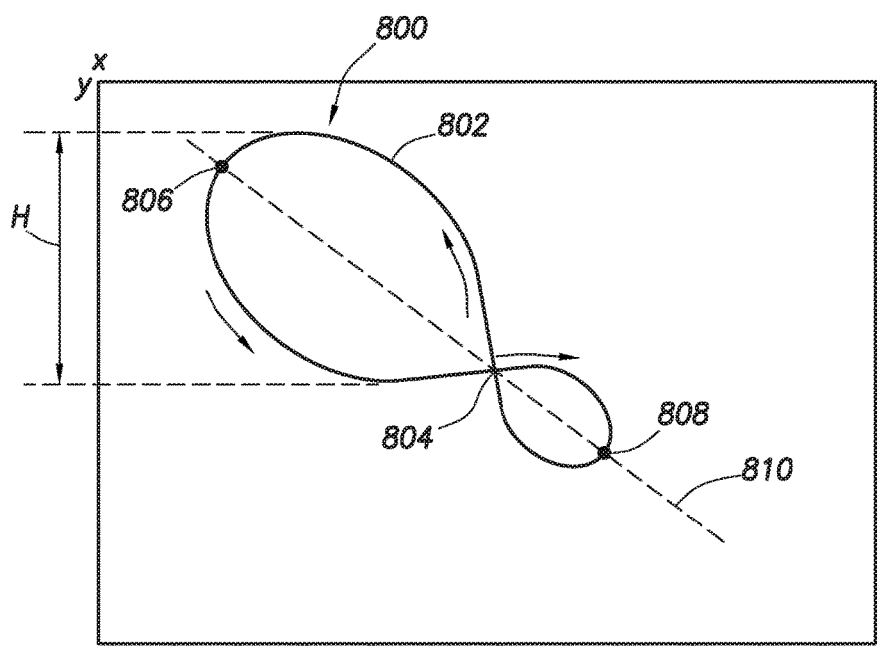
FIG. 8 shows a plot of an example set of pupil position data in the coordinate space of the eye camera in accordance with example embodiments.

Thus, as between the stimulus data and the pupil position data, there may be time alignment issues. Further, some or all the above-noted distortions may be present in the pupil position data. Further still, the example test control system 102 does not know in advance the relationship between pupil position in the frames of the eye camera and gaze location on the computer screen. Thus, the next step in the example cognitive function testing is to correct offsets (both time and positional) as between the stimulus data and the pupil position data. In order to at least partially address the distortions noted above, and further to align the time basis of the pupil position data with respect to the stimulus data, the example systems perform a series of steps. FIG. 8 shows a plot of an example set of pupil position data in the coordinate space of the eye camera. In particular, FIG. 8 shows a distorted lemniscate pattern 800 in the form of line 802. It will be understood that the line merely represents pupil position as function of time in the coordinate space of the eye camera, with time represented by the arrows within the figure. The lemniscate pattern 800 of FIG. 8 shows several example distortions, including rotational distortion possibly caused by rotational misalignment of the eye camera 104, along with distortion as between the left and right lobes possibly caused by the eye camera 104 not being directly aligned with the eye and/or the three-dimensional movement of the eye projected into the two-dimensional coordinate space of the eye camera 104. There may also be time offsets in the data, but such time offsets are not explicitly shown.

In the example system of FIG. 6, the pupil position data created by the eye camera pack 602 (such as shown visually in FIG. 8) is transferred to the portable computer 604, and the further processing performed by the portable computer; however, the various portions of the correcting the offsets between the stimulus data and the pupil position data could be performed by the eye camera pack 602.

Figure 9:
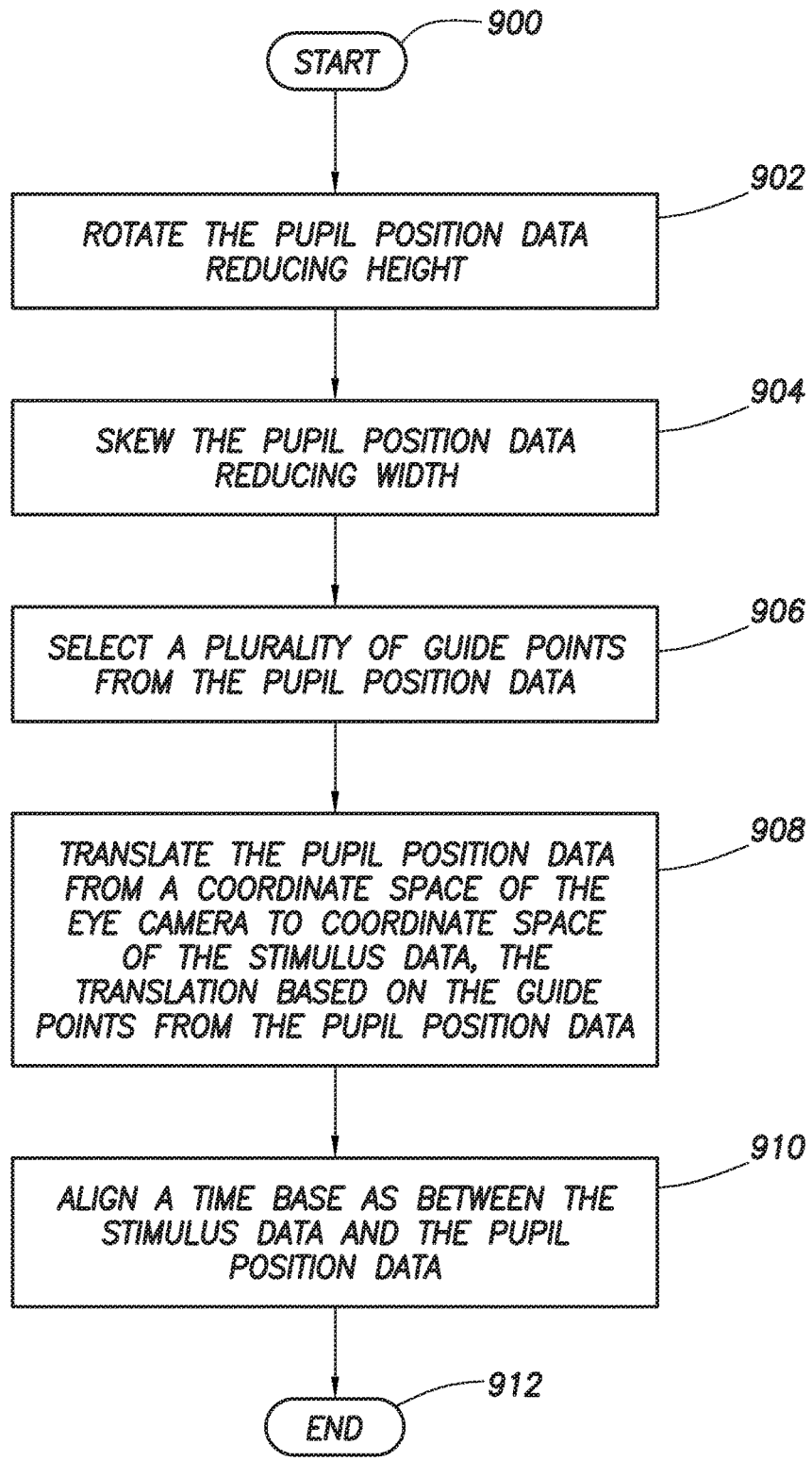
FIG. 9 shows a method in accordance with example embodiments.

FIG. 9 shows a flow diagram of a method that may be used to correct the offsets noted above. In particular, the method starts (block 900) and comprises: rotating the pupil position data reducing height (block 902); skewing the pupil position data reducing width (block 904); selecting a plurality of guide points from the pupil position data (block 906); translating the pupil position data from a coordinate space of the eye camera to coordinate space of the stimulus data, the translation based on the guide points from the pupil position data (block 908); and aligning a time base as between the stimulus data and the pupil position data (block 910). Thereafter the method ends (block 912). Each step will be addressed in turn.

Figure 10:
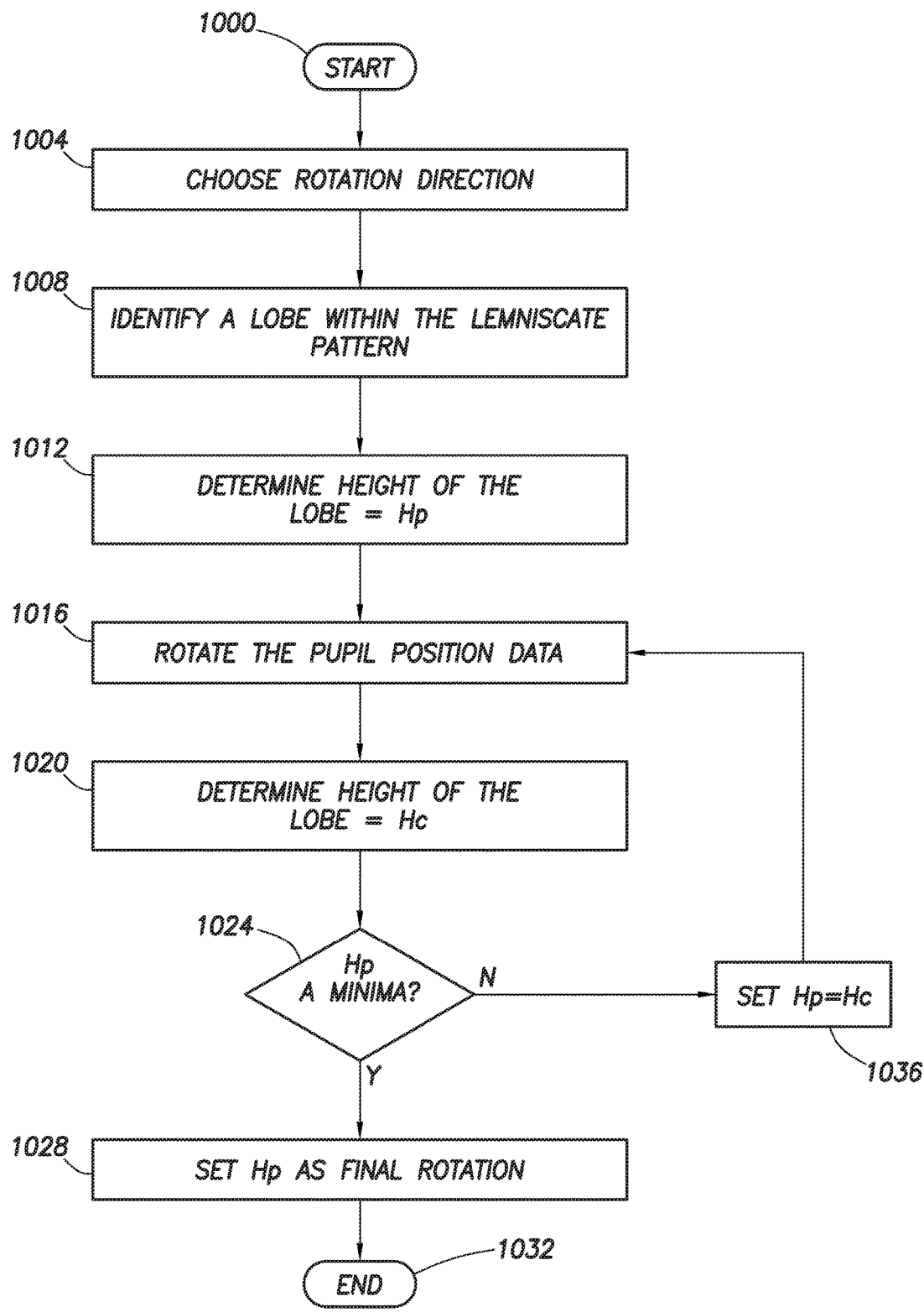
FIG. 10 shows a method in accordance with example embodiments.

The example step of rotating the pupil position data reducing height (block 902) is used to correct for rotational issues associated with camera and/or distortions caused by the three-dimensional movement of the pupil projected into the two-dimensional coordinate space of the eye camera 104. In particular, the pupil position data is rotated about any suitable point, such as the center of the bounding box (e.g., a rectangle whose domain and range encompasses all the data points) that the viewable area of the data, or the center 804 of the lemniscate pattern if such can be identified in the pupil position data. FIG. 10 shows a flow chart of an example method for rotation of the pupil position data to reduce height. In particular, the method starts (block 1000) and proceeds to choosing a rotation direction (block 1004). In the example pupil position data of FIG. 8, the left lobe is rotationally higher than the right lobe, so rotation selected would be counter-clockwise. Of course, based on the circumstances of the cognitive function test the rotation needed could be clockwise. Choosing the rotation direction can take any suitable form. For example, the computer system may determine the outer-most inflection point of the left lobe (the outer-most inflection point in the left lobe in FIG. 8 being point 806) and the outer-most inflection point in the right lobe (the outer-most inflection point in the right lobe in FIG. 8 being point 808) and determining the slope of the line 810. The slope of line 810 thus provides an indication of direction of rotation to make the line horizontal, in the example of FIG. 8 the rotation being counter-clockwise. As another example, the system may compare the X value of the point with the smallest Y value (the "highest" data point) against the value of the center of the bounding box. If the X value is less than the X value for the center of the bounding box (i.e., if the left lobe is higher than the right lobe), then the rotation is counter-clockwise; otherwise, the rotation is clockwise.

Referring simultaneously to FIGS. 8 and 10, regardless of the mechanism to determine the rotational direction, the next step in the example method is to choose or identify a lobe within the lemniscate pattern (block 1008). In one example implementation, the height of the bounding box is determined. The lobe that defines an upper portion (or alternatively lower portion) is selected. For purposes of description, it will be assumed the left lobe of FIG. 8 is chosen, but the example method works equally well if the right lobe is chosen, and also works equally well regardless of whether the larger lobe or smaller lobe is selected. Within the chosen lobe (and for a particular rotation of the pupil position data), the height H of the selected lobe is determined (block 1012), such as the projection of the selected lobe onto the Y axis of the coordinate space. The height of the lobe is set to be the "previous" height Hp for reasons that will become clearer below. The next step in the example method is to rotate the pupil position data in the chosen direction of rotation (block 1016). Next, the example method determines the height of the selected lobe in the rotated data (block 1020), with the height designated as the "current" height Hc. Thereafter, a determination is made as to whether the previous height Hp represents a minima (block 1024). That is, the rotational angle where the height is minimized represents a substantially correct rotation of the pupil position data; however, determining minimized height may be determined only after over rotating the pupil position data to find that the height again begins to increase. Thus, the determination at block 1024 is whether the previous height Hp represents a minima as compared to the current height Hc. If the previous height Hp represents a minima (again block 1024), the next step in the example method is to set the rotational angle represented by the previous height Hp as the final rotation (block 1028), and the example method ends (block 1032).

Returning to decision block 1024, if the previous height Hp does not represent a minima (the N path out of block 1024), then the example system sets the previous height Hp equal to the current height Hc (block 1036), and returns to the next rotation of the pupil position data (block 1016).

In the example method of FIG. 10, it is assumed that small incremental rotations are made until the correct rotation is determined. However, variations of the method are possible. For example, the computer system may rotate the pupil position data through a plurality of rotations (e.g., covering between 90 and 180 rotational degrees), each rotation creating a projected height. Once all the rotations are complete, the computer system may then search the data set of projected height to select the smallest magnitude as representing the desired rotation. As another example, the computer system may make several coarse rotations to find a zone within which the minima may reside, and then within the coarse zone of angles make smaller rotations until the rotation representing the minimum height is identified. Moreover, the embodiments discussed with respect to FIG. 10 find a rotational angle associated with a minimum height. However, in other cases it is not required that a minima be found, and the method may merely find a rotational angle where the height H is reduced significantly, but not necessarily the minima, and yet the cognitive function testing system operate acceptably so long as the pre-injury testing and the post-injury test utilize the same technique for selecting the rotation to reduce height. Finally with respect to the rotation of the pupil position data, depending on point of rotation and the size of the pattern of represented by the pupil position data, the rotation may move a portion of the lemniscate pattern of the pupil position data out of the desired quadrant. Thus, additional translations may be used to center the rotated pupil position data back in the quadrant represented by the coordinate system.

Figure 11:
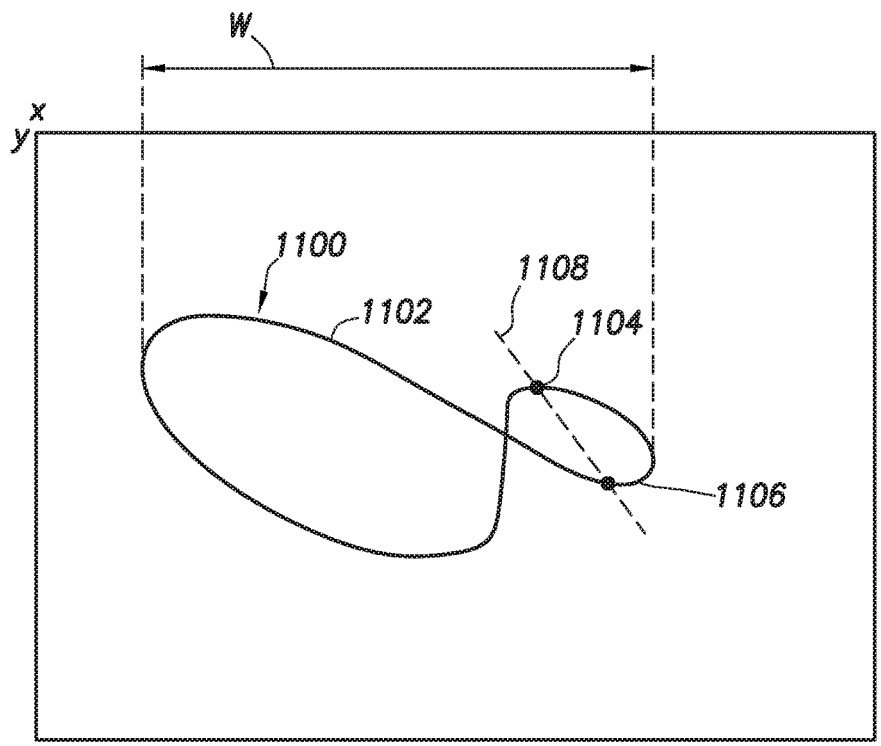
FIG. 11 shows a plot of an example set of pupil position data in the coordinate space of the eye camera after rotation of the data in accordance with example embodiments.

FIG. 11 shows a plot of an example set of pupil position data in the coordinate space of the eye camera after rotation of the data to reduce or minimize height (and possibly after translations to get the lemniscate pattern within the desired quadrant). In particular, FIG. 11 shows a distorted lemniscate pattern 1100 in the form of line 1102. The lemniscate pattern 1100 of FIG. 11, while corrected rotationally according the discussion above, has been modified to emphasize or highlight skew (i.e., a horizontal shifting similar in pattern as a shift from a square to a parallelogram). FIG. 11 also still shows distortion as between the left and right lobes as previously discussed. There may also be time offsets in the data, but such time offsets are not explicitly shown. Referring simultaneously to FIGS. 9 and 11, the next step in the example correction of offsets of FIG. 9 is the skewing the pupil position data to reduce or minimize width (block 904). That is, the pupil position data is adjusted to reduce or remove the skew.

Figure 12:
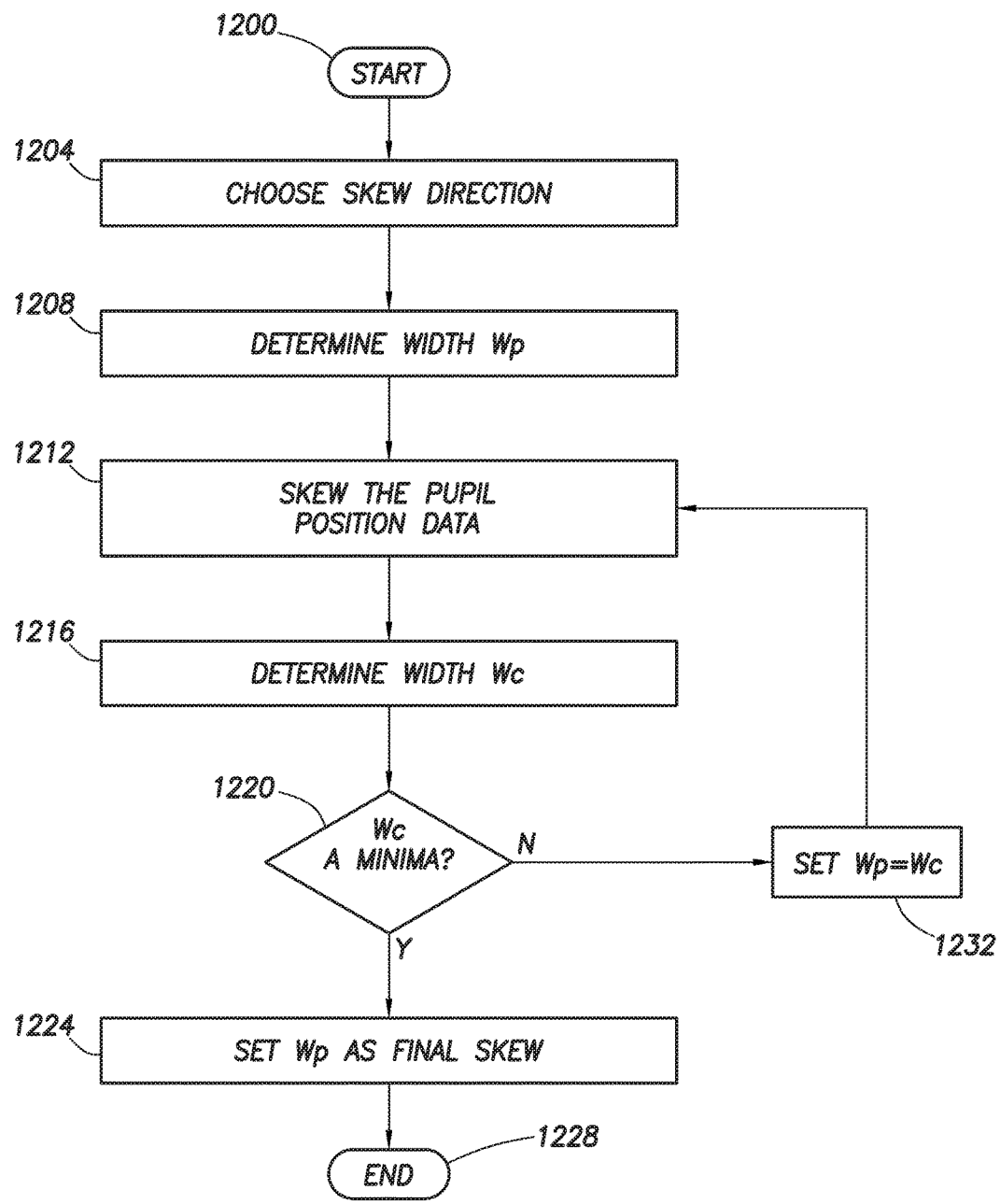
FIG. 12 shows a method in accordance with example embodiments.

FIG. 12 shows a flow chart of an example method for skewing of the pupil position data to reduce width. Referring simultaneously to FIGS. 11 and 12, the method starts (block 1200) and proceeds to choosing a skew direction (block 1204). In the example pupil position data of FIG. 11, the upper portions of the lemniscate pattern are skewed to the left compared to the lower portions of the lemniscate pattern, and thus the correct skew direction is a skewing of the pattern to the right in the view of the FIG. 11. Of course, based on the circumstances of the cognitive function test the skew needed could be the opposite direction. Choosing the skew direction can take any suitable form. For example, the computer system may determine the upper inflection point of the right lobe (the upper inflection point in the right lobe in FIG. 11 being point 1104) and the lower inflection point in the right lobe (the lower inflection point in the right lobe in FIG. 11 being point 1106), and determine the slope of line 1108 between those points. The slope of line 1108 thus providing an indication of direction of skew, in the example situation a skew with the right to make the line vertical. In another example implementation, the Y value of the point with the highest X value is compared against the Y value of the point with the lowest X value. If the first Y value is less than the second Y value (i.e., the top-right portion of the right lobe sticks out more), then the skew is to the left; otherwise, the skew is to the right.

Still referring simultaneously to FIGS. 11 and 12, regardless of the mechanism to determine the skew direction, the next step in the example method is to determine a width W (block 1208) of the lemniscate pattern within the pupil position data, such as the projection of the width of the lemniscate pattern onto the onto the X axis of the coordinate space as shown. The width of the lemniscate pattern is set to be the "previous" width Wp for reasons that will become clearer below. The next step in the example method is to skew the pupil position data in the chosen direction (block 1212). Skewing the pupil position data involves shifting a first horizontal row of the pupil position (e.g., an upper-most row or lowest Y value row) a predetermined amount, and shifting each subsequent horizontal row of the pupil position data (e.g., lower rows in the view of FIG. 11, or higher Y value rows) a predetermined percentage of a distance shift for the immediately previous row. So, for example, an upper most horizontal row may be shifted 100% of the predetermined distance, the immediately subsequent horizontal row may be shifted 99% of the predetermined distance, the next subsequent horizontal row may be shifted 98% of the predetermined distance, and so on until all rows have pupil position data have been shifted (except, perhaps, the last row). Each set of shifting of the rows creates a respective skewed data.

Next, the example method determines the width of the lemniscate pattern in the skewed data (block 1216), with the width designated as the "current" width Wc. Thereafter, a determination is made as to whether the previous width Wp represents a minima (block 1220). That is, the predetermined skew amount where the width is minimized represents a substantially correct skew of the pupil position data; however, determining minimized width may require over skewing the pupil position data to find that the width again begins to increase. Thus, the determination at block 1220 is whether the previous width Wp represents a minima as compared to the current width Wc. If the previous width Wp represents a minima (again block 1220), the next step in the example method is to set the skewed data with width Wp as the final skewed data (block 1224), and the example method ends (block 1228). Stated otherwise, the example method selects, for use in further processing as the pupil position data, the skewed data wherein the horizontal width is reduced or minimized.

Returning to decision block 1220, if the previous width Wp does not represent a minima (the N path out of block 1220), then the example system sets the previous width Wp equal to the current width Wc (block 1232), and returns to the next skew of the pupil position data (block 1212).

In the example method of FIG. 12, it is assumed that small incremental skews of the pupil position data are made until the correct skew is determined. However, variations of the method are possible. For example, the computer system may skew the pupil position data through a plurality of predetermined distances (e.g., covering all the possible skew amounts), each skew creating a projected width. Once all the skews are complete, the computer system may then search the data set of projected widths to select the smallest magnitude as representing the desired skew amount. As another example, the computer system may make several coarse skew amounts to find a zone within which the minima may reside, and then within the coarse zone of skew amounts make smaller skews until the skewing representing the minimum width is identified. Moreover, the embodiments discussed with the respect to FIG. 12 find a skew amount associated with a minimum width. However, in other cases it is not required that a minima be found, and the method may merely find a skew where the width W is reduced significantly, but not necessarily the minima, and yet the cognitive function test system operate acceptably so long as the pre-injury testing and the post injury test utilize the same technique for selecting the skew.

Figure 13:
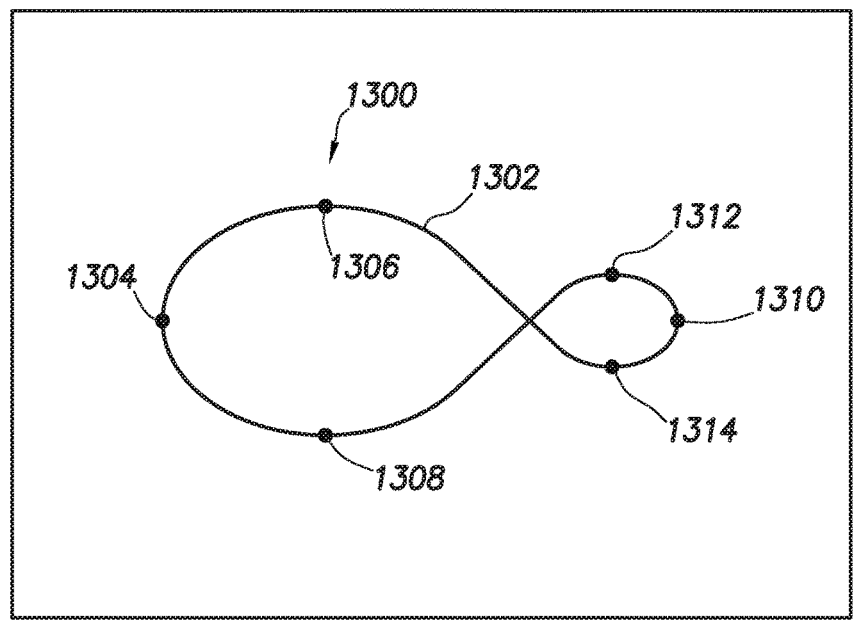
FIG. 13 shows a plot of an example set of pupil position data in the coordinate space of the eye camera after rotation and after skewing of the data in accordance with example embodiments.

FIG. 13 shows a plot of an example set of pupil position data in the coordinate space of the eye camera after rotation (according to FIG. 11) to reduce or minimize height, and after skewing of the data (according to FIG. 12) to reduce or minimize width. In particular, FIG. 13 shows a distorted lemniscate pattern 1300 in the form line 1302. FIG. 13 still shows distortion as between the left and right lobes as previously discussed. There may also be time offsets in the data, but such time offsets are not explicitly shown. Referring simultaneously to FIGS. 9 and 13, the next step in the example correction of offsets of FIG. 9 is to select a plurality of guide points from or within the pupil position data (block 906). In example methods six guide points are selected comprising: a left-most point of a left lobe (point 1304); an upper-most point of the left lobe (point 1306); a lower-most point of the left lobe (point 1308); a right-most point of a right lobe (point 1310); an upper-most point of the right lobe (point 1312); and a lower-most point of the right lobe (point 1314). Additional guide points (e.g., the center crossing point) may be used, or fewer guides may be equivalently used.

The next step in the example method of FIG. 9 is to translate the pupil position data from the coordinate space of the eye camera to the coordinate space of the stimulus data, the translations based on the guide points selected from or within the pupil position data, and a corresponding set of guide points in the stimulus data (FIG. 7). In one example translation, the guide points from the pupil position data and the corresponding guide points from the stimulus data are placed in a matrix, and singular value decomposition is performed. The output matrix of the singular value decomposition represents parameters of a function to perform the translation of the pupil position data into the coordinate space of the stimulus data. Stated slightly differently, the translation performed using the parameters determined by the singular value decomposition translate the geometry of the eye as seen in the eye camera to the coordinate space of the stimulus data. The initial translation of the pupil position data into the coordinate space of the eye camera based on the guide points is an initial translation to assist with aligning the time base as between the different time domains in the eye camera pack 602 and the portable computer 604. However, even in systems such as FIGS. 4 and 5 an initial translation may be used to correct for time base issues caused by time-sliced processing and/or multi-threaded processing.

Still referring to FIG. 9, the next step in the example correction of offsets is to align the time base as between the stimulus data and the pupil position data (with pupil position data translated to the coordinate space of the of the stimulus data) (block 910). Thereafter the example correction of offsets ends (block 912). Aligning the time base between stimulus data and the pupil position data can take any suitable form. One example system involves shifting the time reference for each data point of the pupil position data by a predetermined amount of time (e.g., starting at half the difference between a first point's time stamp and a last point's time stamp (in the example system about 4 seconds)). For the time-shifted pupil position data, the example method then generates a cumulative distance measure between the stimulus data and pupil position data for each corresponding point in time. That is, the cumulative distance measure is the sum of the distances between the points in the stimulus data and points in the pupil position data that correspond in time across the entire time spectrum of interest. The cumulative distance measure may be calculated based on or according to the following equation:

$$CDM = \sum_t \sqrt{(s_x(t) - p_x(t))^2 + (s_y(t) - p_y(t))^2} \qquad (1)$$

where CDM is the cumulative distance measure, $s_x(t)$ and $s_y(t)$ are coordinates of a datum of stimulus data at time t, and $p_x(t)$ and $p_y(t)$ are coordinates of a datum of pupil data at time t. Though Equation (1) indicates a summing over time t, as discussed above the pupil position data may contain 477 points of data at 477 discrete times. In some cases, the time associated with data within the pupil position data may not precisely align with the time associated with data in the stimulus data, and thus the system, in performing the cumulative distance measure calculation, may pick data points closest in time as between the pupil position data and stimulus data.

The shifting and generation of the cumulative distance measure is repeated for a plurality of different predetermined amounts of time, each set of shifting the time reference and generating the cumulative distance measure creates respective time-skewed data. For example, the creation of the cumulative distance measure may be repeated for shifts in time between −4,000 milliseconds (ms) and +4,000 ms with suitable increments (e.g., 1 ms increments, 10 ms increments). In other words, in the example method 477 distance measures are summed 8,000 times. From the plurality of cumulative distance measures, the example system (e.g., the portable computer 604) then selects for use in further processing as the pupil position data, the time-skewed data for which the cumulative distance measure is reduced or minimized. That is, the time skew represented by the lowest cumulative distance measure is applied to the pupil position data in the original coordinate space (i.e., the coordinate space of the eye camera) for reasons that will become more clear below, and the time-skewed data in the original coordinate space becomes the pupil position data used in the further processing.

The pupil position data at this stage in the implementation has been corrected for offsets by being rotated, distance skewed, and had its time domain aligned with the time domain of the stimulus data. The next step in the example method is to again translate the modified/adjusted pupil position data from the coordinate space of the eye camera to the coordinate space of the stimulus data. As the reader will note, in the example method described to this point a set of pupil position data has already been translated from the coordinate space of the eye camera to the coordinate space of the stimulus data as a precursor to selecting a time offset used to align time as between the data sets; however, the previous translation was based on guide point locations in the respective coordinate spaces that likely did not correspond in time, and thus the initial translation likely had error. However, for purposes of aligning time domains as between the stimulus data and the pupil position data the initial translation is sufficient.

So again, the next step in the example method is to translate the modified/adjusted pupil position data from the coordinate space of the eye camera to the coordinate space of the stimulus data. Thus, the next step in the example method is to select a plurality of guide points from or within the pupil position data. As before, in the example methods six guide points are selected comprising: a left-most point of a left lobe; an upper-most point of the left lobe; a lower-most point of the left lobe; a right-most point of a right lobe; an upper-most point of the right lobe; and a lower-most point of the right lobe. Additional guide points (e.g., the center crossing point) may be used, or fewer guides may be equivalently used. Unlike the first selection and translation, the guide points selected in the (offset corrected) pupil position data correspond in time to the equivalent guide points selected in the stimulus data. Thereafter, the example method translates the (offset corrected) pupil position data from the coordinate space of the eye camera to the coordinate space of the stimulus data, the translations based on the guide points selected from or within the pupil position data, and a corresponding set of guide points in the stimulus data. As before, in the example method the guide points from the pupil position data and the corresponding guide points from the stimulus data are placed in a matrix, and singular value decomposition is performed. The output matrix of the singular value decomposition represents parameters of a function to perform the translation of the pupil position data into the coordinate space of the stimulus data, and thus the function is used to translation the pupil position data.

The example method then generates a cumulative distance measure between the stimulus data and pupil position data for each corresponding point in time. As before, the cumulative distance measure is the sum of the distances between the points in the stimulus data and points in the pupil position data that correspond in time across the entire data set, such as a cumulative distance measure discussed with respect to Equation (1) above. Stated otherwise, the example method generates a test score being the cumulative distance between the stimulus data and the pupil position data for each corresponding point in time. If the patient was able to follow the visual cue perfectly, then the test score will be low to zero, but in practice such a result is improbable. The patient cannot perfectly anticipate the path of travel of the visual cue (particularly when the path abuts the left-most and right-most portions of the computer screen). Moreover, subtle head movements, the patient blinking during the test, etc. will in most cases result in a non-zero distance-measure test score. Nevertheless, the test score is thus a value that represents a cumulative distance that the patient's gaze was off with respect to the location of the visual cue over the course of the cognitive function test.

The example method may then proceed to calculating an indication of cognitive function based on the test score, and in some cases displaying the indication of cognitive function. In some cases, the indication of cognitive function may be the test score itself. In other cases, the indication of cognitive function may be based on a pre-injury cognitive function test for the patient, or may be based on a plurality of indications of cognitive function of other individuals. That is in cases where there is a baseline or pre-injury cognitive function test, calculating the indication of cognitive function may be based on a change of cognitive function as between the pre-injury cognitive function test and the post-injury cognitive function test. In other cases, however, a community baseline and/or community average may help inform the calculation of cognitive function based on the test score.

Figure 14:
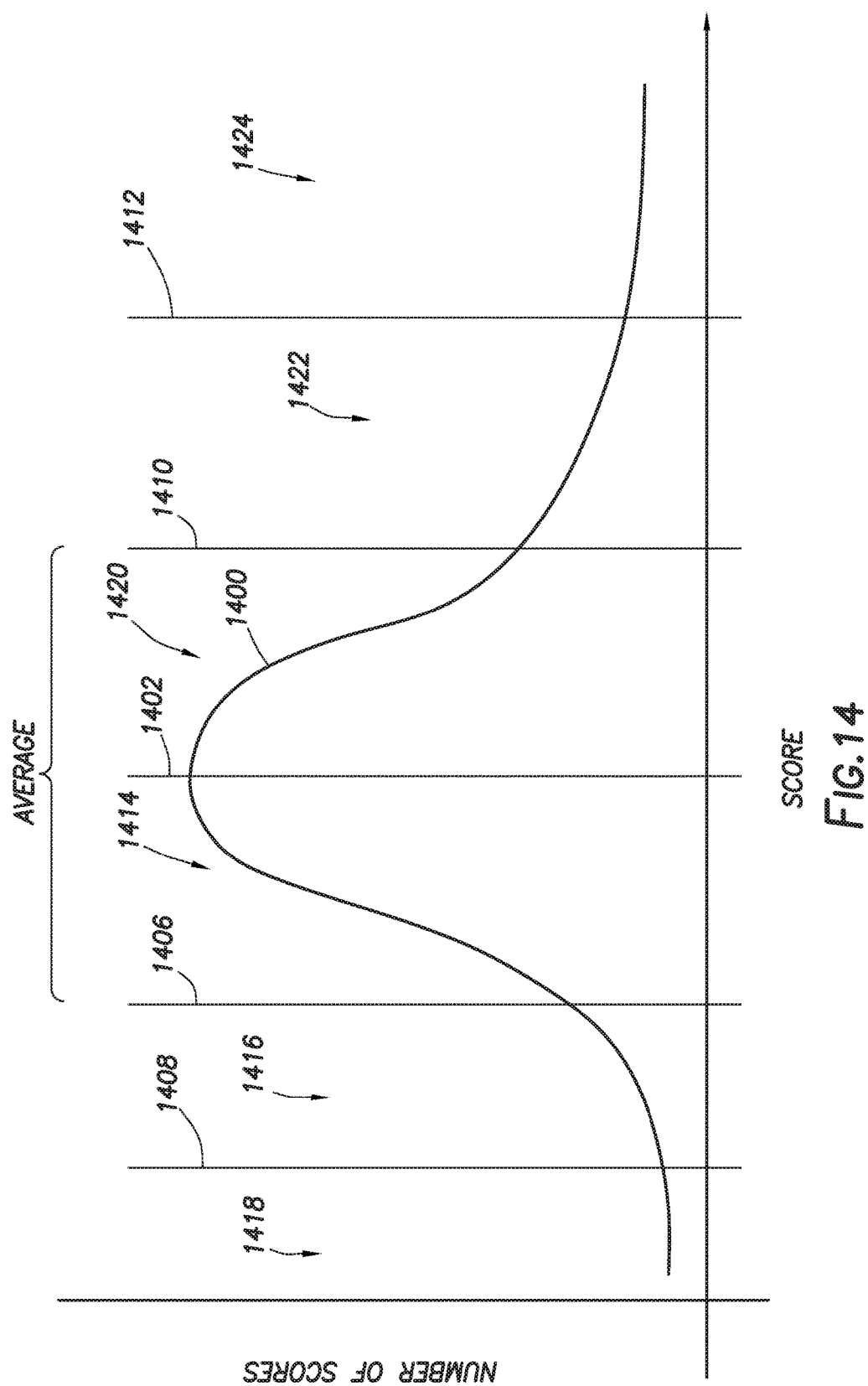
FIG. 14 shows a distribution of test scores in accordance with example embodiments.

FIG. 14 shows an example distribution of test scores of cognitive function testing. In particular, FIG. 14 shows test score along the X axis plotted against number of tests on the Y axis. Cognitive function testing for a group of patients results in a Gaussian or normal distribution of test scores when the sample size is sufficiently large, the normal distribution shown in FIG. 14 as line 1400. A normal distribution has a mean or mode, illustrated by line 1402, as well as a set of gradations delineated by standard deviations from the mean. The example of FIG. 14 shows first standard deviation 1406 above the mean (in this case "above" representing better (lower) test scores) and a second standard deviation 1408 above the mean. Likewise, the example of FIG. 14 shows a first standard deviation 1410 below the mean and a second standard deviation 1412 below the mean. In accordance with example embodiments, the standard deviations conceptually create impairment ranges or zones. For example the area between the mean 1402 and the first standard deviation 1406 above the mean conceptually creates an impairment zone. The remaining standard deviations thus define the further impairment zones 1416, and 1418 above the mean, and impairment zones 1420, 1422, and 1424 below the mean.

With the idea of the impairment zones associated with the normal distribution in mind, the specification now turns to a discussion of calculating an indication of cognitive function based on the test score using the community baselines. In particular, in some example embodiments the indication of cognitive function is based not only on pre-injury and post-injury test scores, but also on how much the pre-injury and post-injury test scores relate to the community baseline, and more particularly to the impairment ranges indicated within the community. That is, in some embodiments, the distance or difference between the pre-injury test score and the post-injury test score in terms of impairment ranges defines a Boolean calculation as to impairment. More particularly, if the post-injury test score is two or more impairment ranges (stated otherwise, two or more standard deviations) away from the pre-injury test score, then the calculation of the indication of cognitive function may indicate significant impairment. For example, if in a pre-injury test a patient's test score falls in impairment range 1414, and in a post-injury test the test score falls within impairment range 1422, then impairment may be indicated. It is noted, however, that impairment is not necessarily indicated by being far to the right of the mean. Consider, as another example, a pre-injury test score for a patient falling impairment range 1418, and a post-injury test score falling in impairment range 1420. Even though the post-injury test score is still within one standard deviation of the mean, the change from impairment range 1418 (lowest pre-injury score, highest cognitive function) for a patient to an effectively average score may still represent significant impairment, and thus in example systems impairment may still be indicated.

FIG. 14 shows six impairment ranges so as not to unduly complicate the figure. However, the inventors of the present specification have found that, based on data from actual patients, nine impairment ranges from the community baseline provides a robust system. The nine impairment ranges include an average impairment range (being two standard deviations wide and centered over the mean), three impairment ranges above the mean, and five impairment ranges below the mean. Further with respect to FIG. 14, using community baselines for calculating the indication of cognitive function means that the indication of cognitive function may be based on a plurality of other individuals. In some cases, however, the patient's pre-injury test score may be included in the community baseline, but in others the patients pre-injury test score may be omitted.

In various embodiments the community baseline data may be accessed by the testing control system 102 by accessing a remote database 116 over the internet 118 (FIG. 1). Further still, in example systems each test score generated by the testing control system 102 is uploaded (e.g., at the time of testing, or periodically) to the database 116 to help expand and refine the community baseline data (and thus the determination of standard deviation and impairment ranges).

Figure 15:
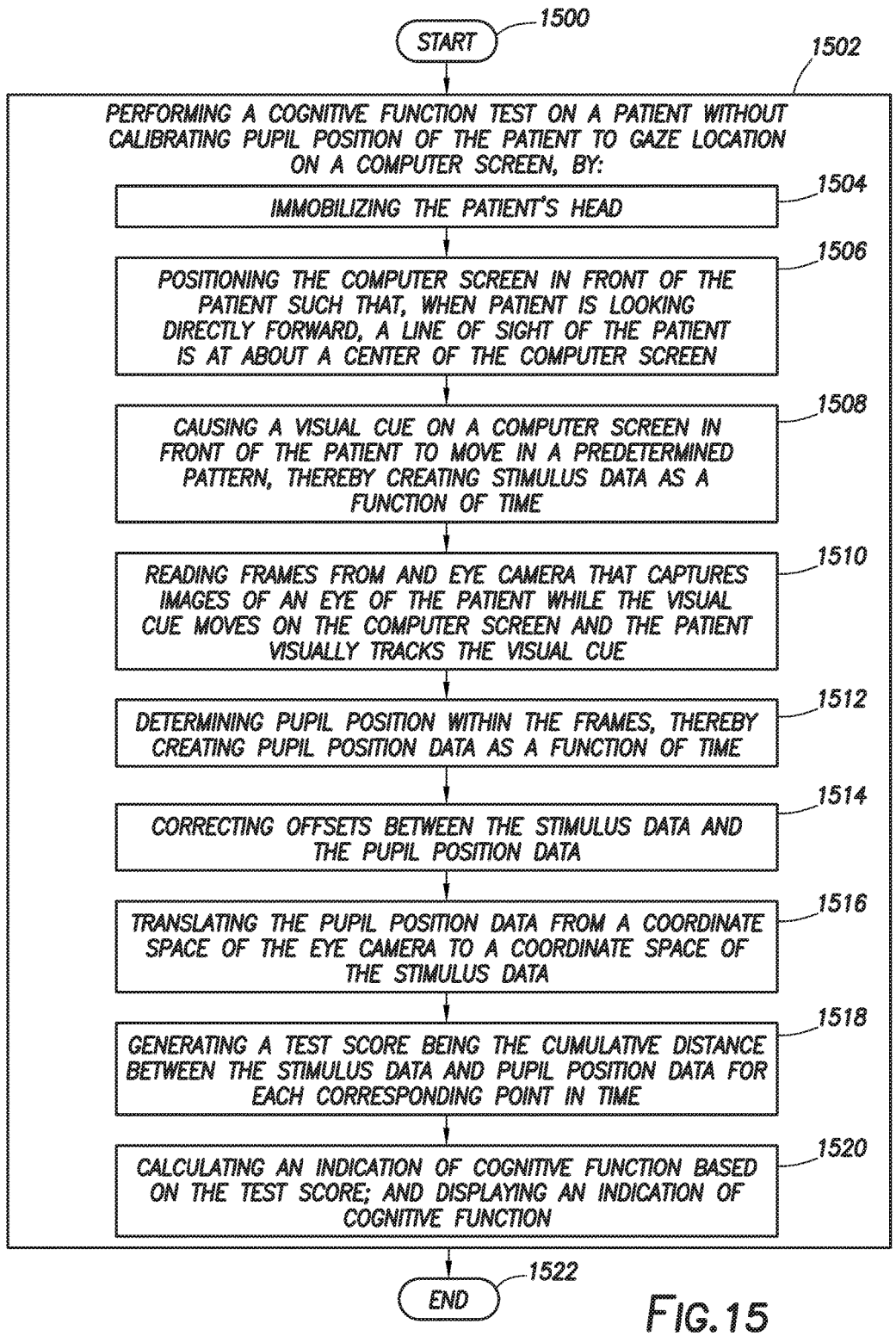
FIG. 15 shows a method in accordance with example embodiments.

FIG. 15 shows a method in accordance with at least some embodiments. In particular, the method starts (block 1500) and proceeds to performing a cognitive function test on a patient without calibrating pupil position of the patient to gaze location on a computer screen (block 1502). The performing may comprise: immobilizing the patient's head (block 1504); positioning the computer screen in front of the patient such that, when patient is looking directly forward, a line of sight of the patient is at about a center of the computer screen (block 1506); causing a visual cue on a computer screen in front of the patient to move in a predetermined pattern, thereby creating stimulus data as a function of time (block 1508); reading frames from an eye camera that captures images of an eye of the patient while the visual cue moves on the computer screen and the patient visually tracks the visual cue (block 1510); determining pupil position within the frames, thereby creating pupil position data as a function of time (block 1512); correcting offsets between the stimulus data and the pupil position data (block 1514); translating the pupil position data from a coordinate space of the eye camera to a coordinate space of the stimulus data (block 1516); generating a test score being the cumulative distance between the stimulus data and pupil position data for each corresponding point in time (block 1518); calculating an indication of cognitive function based on the test score; and displaying an indication of cognitive function (block 1520). Thereafter, the illustrative method may end (block 1522).

The above discussion is meant to be illustrative of the principles and various embodiments of the present invention. Numerous variations and modifications will become apparent to those skilled in the art once the above disclosure is fully appreciated. For example, for patients for whom no pre-injury test scores are available, the calculation of the indication of impairment may still be based on the community baseline, with the understanding that uncertainly may still exist. For example, if the patient's test score falls in the right-most impairment range (i.e., severely impaired), then the calculation of cognitive function may indicate impairment with fairly high certainty, but if the patient's test score falls into the first impairment range to the right of average, impairment may still be present. It is intended that the following claims be interpreted to embrace all such variations and modifications.

What is claimed is:

1. A method comprising:
   performing a cognitive function test on a patient, the performing by:
   immobilizing the patient's head;
   positioning the computer screen in front of the patient such that, when patient is looking directly forward, a line of sight of the patient is at about a center of the computer screen;
   causing, by a computer system, a visual cue on a computer screen in front of the patient to move in a predetermined pattern, thereby creating stimulus data as a function of time;
   reading, by a computer system, frames from an eye camera that captures images of an eye of the patient while the visual cue moves on the computer screen and the patient visually tracks the visual cue;
   determining, by a computer system, pupil position within the frames, thereby creating pupil position data as a function of time, the pupil position data in a coordinate space of the eye camera;
   correcting, by a computer system, offsets by rotating the pupil position data reducing height, and skewing the pupil position data reducing width, the correcting creates modified pupil position data in the coordinates space of the eye camera;
   translating, by a computer system, the modified pupil position data from the coordinate space of the eye camera to a coordinate space of the stimulus data;
   generating, by a computer system, a test score being a cumulative distance between the stimulus data and modified pupil position data for each corresponding point in time;
   calculating, by a computer system, an indication of cognitive function based on the test score; and
   displaying, by a computer system, an indication of cognitive function.

2. The method of claim 1 wherein the cognitive function test is at least one selected from the group consisting of: concussion testing; drug-induced impairment testing; and autism spectrum disorder testing.

3. The method of claim 1 wherein positioning the computer screen further comprises positioning the computer screen about two feet from the patient's eyes.

4. The method of claim 1 wherein causing the visual cue to move further comprises causing the visual cue to move in a lemniscate pattern.

5. The method of claim 4 wherein causing the visual cue to move further comprises causing the visual cue to abut a left-most portion of the computer screen during a first portion of the lemniscate pattern, and causing the visual cue to abut a right-most portion of the computer screen during a second portion of the lemniscate pattern.

6. The method of claim 1 wherein reading frames from the eye camera further comprises at least one selected from the group consisting of:
   reading by the eye camera being part of a headset; and
   reading from the eye camera being coupled to a chin rest.

7. The method of claim 1 wherein correcting offsets further comprises:
   selecting a plurality of guide points from the pupil position data;
   translating the pupil position data from the coordinate space of the eye camera to the coordinate space of the stimulus data, the translating based on the guide points from the pupil position data, and the translating creates temporary data;
   determining a time skew between the stimulus data and the temporary data; and
   aligning a time base as between the stimulus data and the pupil position data in the coordinate space of the eye camera based on the time skew.

8. The method of claim 1 wherein rotating the pupil position data further comprises rotating the pupil position data minimizing height.

9. The method of claim 1 wherein skewing the pupil position data further comprises skewing the pupil position data minimizing width.

10. The method of claim 9 wherein skewing the pupil position data further comprises:
    shifting a first horizontal row of the pupil position data a predetermined distance;
    shifting each subsequent horizontal row of the pupil position data a predetermined amount of a distance shift for the immediately previous row;
    repeating the shifting steps for a plurality of predetermined distances, each set of shifting steps creates respective skewed data; and then
    selecting, for use in further processing as the pupil position data, the skewed data wherein the horizontal width is minimized.

11. The method of claim 7 wherein selecting the plurality of guide points of the pupil position data further comprises selecting: a left-most point of a left lobe; an upper point of the left lobe; a lower point of the left lobe; a right-most point of a right lobe; an upper point of the right lobe; a lower point of the right lobe.

12. The method of claim 7 wherein aligning determining the time skew between the stimulus data and the temporary data further comprises:
    shifting a time reference for each data point of the temporary data by a predetermined amount of time; and then
    generating a cumulative distance measure between the stimulus data and temporary data for each corresponding point in time;
    repeating the shifting and generation of the cumulative distance measure for a plurality of predetermined amounts of time, each set of shifting the time reference and generating the cumulative distance measure creates respective time-skewed data; and then
    selecting the time skew for which the cumulative distance measure is reduced.

13. The method of claim 1 wherein calculating an indication of cognitive function based on the test score further comprises comparing the indication of cognitive function to a previous indication of cognitive function for the patient.

14. The method of claim 1 wherein calculating the indication of cognitive function based on the test score further comprises calculating the indication of cognitive function based on a plurality of indications of cognitive function of other individuals.

15. The method of claim 1 wherein calculating the indication of cognitive function further comprises determining, by a computer system, impaired cognitive function of the patient based on a change of at least two standard deviations of the indication of the of cognitive function of the patient, the standard deviation ranges based on a plurality of indications of cognitive function of other individuals.

16. The method of claim 1 wherein immobilizing the patient's head further comprises immobilizing by way of a chin rest with forehead strap.

17. A system for performing cognitive function testing, the system comprising:
    a computer screen;
    an eye camera;
    a means for performing the cognitive function testing coupled to both the computer screen and the eye camera, wherein the means for performing causes the system to:
        move a visual cue on the computer screen in a predetermined pattern, and simultaneously create stimulus data as a function of time;
        read frames from the eye camera while the visual cue moves on the computer screen;
        determine pupil position within the frames, thereby creating pupil position data as a function of time and in a coordinate space of the eye camera;
        correct offsets by rotation of the pupil position data reducing height, and skewing of the pupil nposition data reducing, the correction creates modified pupil position data in the coordinate space of the eye camera;
        translate the modified pupil position data from the coordinate space of the eye camera to a coordinate space of the stimulus data;
        generate a test score being a cumulative distance between the visual cue data and modified pupil position data for each corresponding point in time; and
        calculate an indication of cognitive function based on the test score.

18. The system of claim 17 wherein the cognitive function testing implemented by the means for performing further comprises at least one selected from the group consisting of: concussion testing; drug-induced impairment testing; and autism spectrum disorder testing.

19. The system of claim 17 wherein when the means for performing moves the visual cue, the means for performing moves the visual cue in a lemniscate pattern.

20. The system of claim 19 wherein when the means for performing moves the visual cue causing the visual cue in the lemniscate pattern, the means for performing moves the visual cue such that the visual cue abuts a left-most portion of the computer screen during a first portion of the lemniscate pattern, and the visual cue abuts a right-most portion of the computer screen during a second portion of the lemniscate pattern.

21. The system of claim 17 wherein when the means for performing reads frames from the eye camera, the means for performing implements at least one selected from the group consisting of: read from the eye camera being part of a headset; and read from the eye camera being coupled to a chin rest.

22. The system of claim 17 wherein when the means for performing corrects offsets, the means for performing:

selects a plurality of guide points from the pupil position data;
translates the pupil position data from the coordinate space of the eye camera to the coordinate space of the stimulus data, the translation based on the guide points from the pupil position data and the translation creates temporary data;
determine a time skew between the stimulus data and the temporary data; and
aligns a time base as between the stimulus data and the pupil position data in the coordinate space of the eye camera using the time skew.

23. The system of claim 17 wherein when the means for performing rotates the pupil position data, the means for performing rotates the pupil position data minimizing height.

24. The system of claim 17 wherein when the means for performing skews the pupil position data, the means for performing skews the pupil position data minimizing width.

25. The system of claim 24 wherein when the means for performing skews the pupil position data, the means for performing:
    shifts a first horizontal row of the pupil position data a predetermined distance;
    shifts each subsequent horizontal row of the pupil position data a predetermined amount of a shift for the immediately previous row;
    repeats the shifting steps for a plurality of predetermined distances, each set of shifting steps creates respective skewed data; and then
    selects, for use in further processing as the pupil position data, the skewed data wherein the horizontal width is minimized.

26. The system of claim 22 wherein when the means for performing selects the plurality of guide points, the means for performing selects: a left-most point of a left lobe; an upper point of the left lobe; a lower point of the left lobe; a right-most point of a right lobe; an upper point of the right lobe; a lower point of the right lobe.

27. The system of claim 22 wherein when the means for performing determines the time skew between the stimulus data and the temporary data, the means for performing:
    shifts a time reference for each data point of the temporary data by a predetermined amount of time; and then
    generates a cumulative distance measure between the stimulus data and temporary data for each corresponding point in time;
    repeats the shifting and generation of the cumulative distance measure for a plurality of predetermined amounts of time, each set of shifting the time reference and generation of the cumulative distance measure creates respective time-skewed data; and then
    selects the time skew for which the cumulative distance measure is reduced.

28. The system of claim 17 wherein when the means for performing calculates the indication of cognitive function based on the test score, the means for performing compares the indication of cognitive function to a previous indication of cognitive function for the patient.

29. The system of claim 17 wherein when the means for performing calculates the indication of cognitive function based on the test score, the means for performing compares the indication of cognitive function to a plurality of indications of cognitive function of other individuals.

30. The system of claim 17 where when the means for performing calculates the indication of cognitive function based on the test score, the means for performing determines impaired cognitive function of the patient based on a change of at least two standard deviations of the indication of the of cognitive function of the patient, the standard deviation ranges based on a plurality of indications of cognitive function of other individuals.

31. A system comprising:
a first computer system comprising a first processor, a first memory coupled to the first processor, and a computer screen coupled to the first processor;
a second computer system comprising a second processor, a second memory coupled to the second processor, and an eye camera coupled to the second processor, the second computer system communicatively coupled to the first processor;
wherein the first memory stores a program that, when executed by the first processor, causes the first processor to:
move a visual cue on the computer screen in a lemniscate pattern, and simultaneously create stimulus data as a function of time;
receive pupil position data from the second computer system, the pupil position data in a coordinate space of the eye camera;
correct offsets by causing the first processor to:
rotate the pupil position data reducing, height;
skew the pupil position data reducing width;
select a plurality of guide points from the pupil position data;
translate the pupil position data from the coordinate space of the eye camera to the coordinate space of the stimulus data, the translation based on the guide points from the pupil position data, the translation creates temporary data in the coordinate space of the stimulus data, and the pupil position data in the coordinate space of the eye camera preserved;
determine a time skew between the stimulus data and the temporary data; and
align a time base as between the stimulus data and the pupil position data in the coordinate space of the eye camera using the time skew, the rotation, skew, and alignment create corrected pupil position data in the coordinate space of the eye camera;
translate the corrected pupil position data from the coordinate space of the eye camera to the coordinate space of the stimulus data;
generate a test score being a cumulative distance between the stimulus data and corrected pupil position data for each corresponding point in time; and
calculate an indication of cognitive function based on the test score;

wherein the second memory stores a program that, when executed by the second processor, causes the second processor to:
read frames from the eye camera in operational relationship to a patient's eye while the visual cue moves on the computer screen;
determine pupil position within the frames, thereby the creating pupil position data as a function of time; and
send the pupil position data to the first processor.

32. The system of claim 31 wherein first processor skews the pupil position data, the program causes the first processor to:
shift a first horizontal row of the pupil position data a predetermined distance;
shift each subsequent horizontal row of the pupil position data a predetermined amount of a shift for the immediately previous row;
repeat the shifting steps for a plurality of predetermined distances, each set of shifting steps creates respective skewed data; and then
select, for use in further processing as the pupil position data, the skewed data wherein the horizontal width is minimized.

33. The system of claim 31 wherein when the first processor aligns the time base as between the stimulus data and the pupil position data to create the corrected pupil position data in the coordinate space of the eye camera, the program causes the first processor to:
shift a time reference for each data point of the temporary data by a predetermined amount of time; and then
generate a cumulative distance measure between the stimulus data and temporary data for each corresponding point in time;
repeat the shifting and generation of the cumulative distance measure for a plurality of predetermined amounts of time, each set of shifting the time reference and generation of the cumulative distance measure creates respective time-skewed data; and then
select the time skew for which the cumulative distance measure is reduced.

34. The system of claim 31 wherein when the first processor calculates the indication of cognitive function based on the test score, the program causes the first processor to compare the indication of cognitive function to a previous indication of cognitive function for the patient.

35. The system of claim 31 wherein when the first processor calculates the indication of cognitive function based on the test score, the program causes the first processor to calculate the indication of cognitive function to a plurality of indications of cognitive function of other individuals.

* * * * *